(12) United States Patent
Pascal, Sr.

(10) Patent No.: US 9,078,839 B1
(45) Date of Patent: Jul. 14, 2015

(54) TREATMENT OF ASHY SKIN BY A TOPICAL COMPOSITION AND METHODS OF MANUFACTURE THEREOF

(71) Applicant: Christian D Pascal, Sr., Riverdale, NJ (US)

(72) Inventor: Christian D Pascal, Sr., Riverdale, NJ (US)

( * ) Notice: Subject to any disclaimer, the term of this patent is extended or adjusted under 35 U.S.C. 154(b) by 0 days.

(21) Appl. No.: 14/462,627

(22) Filed: Aug. 19, 2014

Related U.S. Application Data

(60) Provisional application No. 61/875,743, filed on Sep. 10, 2013.

(51) Int. Cl.
| | | |
|---|---|---|
| *A61K 36/00* | (2006.01) | |
| *A61K 36/9066* | (2006.01) | |
| *A61K 36/54* | (2006.01) | |
| *A61K 36/889* | (2006.01) | |
| *A61K 36/886* | (2006.01) | |
| *A61K 8/92* | (2006.01) | |
| *A61K 8/36* | (2006.01) | |
| *A61K 8/58* | (2006.01) | |
| *A61Q 19/00* | (2006.01) | |

(52) U.S. Cl.
CPC ............... *A61K 8/922* (2013.01); *A61K 8/361* (2013.01); *A61K 8/585* (2013.01); *A61Q 19/007* (2013.01); *A61K 2800/30* (2013.01)

(58) Field of Classification Search
CPC ... A61K 36/00; A61K 36/9066; A61K 36/54; A61K 36/889; A61K 36/886
USPC ............. 424/727, 744, 768, 78.02, 777
See application file for complete search history.

(56) References Cited

U.S. PATENT DOCUMENTS

| | | | |
|---|---|---|---|
| 8,318,222 B2 | 11/2012 | Hines et al. | |
| 2004/0234468 A1 | 11/2004 | Kerschner | |
| 2005/0058672 A1* | 3/2005 | Gupta | 424/401 |
| 2006/0257845 A1 | 11/2006 | Kazmi et al. | |
| 2007/0003511 A1 | 1/2007 | Schulz et al. | |
| 2010/0143446 A1 | 6/2010 | Rabouille | |
| 2011/0052523 A1 | 3/2011 | Moriya et al. | |
| 2011/0318453 A1 | 12/2011 | Suganuma et al. | |
| 2012/0040931 A1 | 2/2012 | Kamei | |
| 2013/0022685 A1* | 1/2013 | Sample et al. | 424/498 |

FOREIGN PATENT DOCUMENTS

| | | |
|---|---|---|
| WO | 2008145747 A2 | 12/2008 |
| WO | 2013006336 A2 | 1/2013 |

OTHER PUBLICATIONS

Amazon.com;Lotions for Ashy Skin:Beauty, Jul. 22, 2014http://www.amazon.com/s/ref=nb_sb_noss?url=search-alias=beauty&field-leywords=lotions.

* cited by examiner

*Primary Examiner* — Chris R Tate
*Assistant Examiner* — Deborah Davis
(74) *Attorney, Agent, or Firm* — Werschulz Patent Law, LLC

(57) ABSTRACT

A topical preparation for treating ashy skin and a method of manufacture thereof. The topical preparation is a single phase, hydrophobic, lipophilic preparation comprising plant-based butters that have a melting point around the temperature of the skin surface. The melting point of the mixture is stabilized by a tempering process, minimizing polymorphism. The topical preparation is applied to skin having an ashy appearance and is absorbed into the top layers without leaving a white residue. The topical preparation is translucent, non-irritating and has natural sunscreen properties.

3 Claims, No Drawings

TREATMENT OF ASHY SKIN BY A TOPICAL COMPOSITION AND METHODS OF MANUFACTURE THEREOF

CROSS-REFERENCE TO RELATED APPLICATIONS

This application is a nonprovisional utility application of the provisional patent application, Ser. No. 61/875,743 filed in the United States Patent Office on Sep. 10, 2013 and claims the priority thereof and is expressly incorporated herein by reference in its entirety

TECHNICAL FIELD

The present disclosure relates generally to a topical composition for treating skin ashiness. More particularly, the present disclosure relates to a topical preparation for treating ashy skin and a method of manufacture thereof.

BACKGROUND

Dark-skinned people who have a high amount of melanin in the skin have a problem with skin ashing also known as ashy skin, keratinized dehydrated disorder, xerosis or asteatosis. Ashy skin is commonly found on arms, elbows, lower legs, knees and heels. Ashy skin is generally dry skin that has a dull, white or gray appearance.

Soap residue and white creams can increase the problem. In particular, many creams and lotions intended for moisturizing ashy skin have titanium dioxide, which dries to a light powder leaving a whitish residue on the areas where ashy skin is a problem. These creams and lotions are emulsions, that is, two-phase mixtures of water with oils and fats that require surfactants to stabilize the mixture, preventing the water and fats from separating into separate phases. The fats and fat derivatives are also solids with high melting temperatures so that a residue remains when the water evaporates. These surfactants and high-melting fats also leave a gray to white residue that adds to the ashy appearance.

While these creams and lotion may be suitable for moisturizing, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a topical preparation for treating ashy skin that does not leave a visible residue. Accordingly, the present disclosure provides a topical preparation that lacks hydrophilic ingredients that leave a white residue on the skin surface when the preparation is absorbed into the skin.

Another aspect of an example embodiment in the present disclosure is to provide a topical preparation for treating ashy skin that is easily absorbed by the skin. Accordingly, the present disclosure provides a topical preparation that is a liquid or liquefies at around skin surface temperature, so that the preparation is a liquid when topically applied allowing for easy absorption by the skin.

A further aspect of an example embodiment in the present disclosure is to provide a topical preparation for treating ashy skin that liquefies upon application to skin surface. Accordingly, the present disclosure provides a topical preparation that has a plurality of ingredients, each ingredient a liquid or having a melting point around skin surface temperature, so that the topical preparation is a liquid after application to the skin.

Yet another aspect of an example embodiment in the present disclosure is to provide a topical preparation for treating ashy skin that is lipophilic and single phase. Accordingly, the present disclosure provides a topical preparation that has a plurality of lipophilic, hydrophobic, substantially anhydrous ingredients, all ingredients in a single phase without requiring a surfactant to form an emulsion.

Yet a further aspect of an example embodiment in the present disclosure is to provide a topical preparation for treating ashy skin that is in physically stable form, having a consistent melting point. Accordingly, the present disclosure provides a topical preparation formed by tempering, so that crystallization is controlled by cooling to minimize polymorphism, which creates varying melting temperatures.

Accordingly, the present disclosure describes a topical preparation for treating ashy skin and a method of manufacture thereof. The topical preparation is a single phase, hydrophobic, lipophilic preparation comprising plant-based butters that have a melting point around the temperature of the skin surface. The melting point of the mixture is stabilized by a tempering process. The topical preparation is applied to skin having an ashy appearance and is absorbed into the top layers without leaving a white residue.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. Variations are contemplated as being part of the disclosure.

DETAILED DESCRIPTION OF THE PREFERRED EMBODIMENTS

Herein is described a treatment for ashy skin, also know as keratinized dehydrated disorder, xerosis or asteatosis. The treatment is a topical preparation that is transparent, non-greasy feeling and readily absorbed by the skin. Unlike other moisturizers, the topical preparation is not an oil in water emulsion nor a water in oil emulsion, but it is a completely lipophilic, single-phase homogenous mixture having no added water, no aqueous solutions and no polar components.

As a single-phase preparation, there are no surfactants, emulsifiers or dispersing agents required, reducing the potential for skin irritation. The lipophilic, single-phase homogenous composition provides an essentially non-irritating topical preparation.

The transparent topical preparation leaves no residue and was intentionally formulated without titanium oxide and other whiteners and brighteners typically found in cosmetic preparations that leave white and grayish residues on the skin.

The preparation is substantially absorbed by the skin, giving a non-greasy perception and appearance, transparent and without residue because it is a single-phase mixture without surfactants, emulsifiers, dispersing agents, whiteners, brighteners and water-soluble compounds.

Surfactants, emulsifiers, dispersing agents, whiteners, brighteners and water-soluble compounds produce a solid white residue on the skin when the water in a two-phase emulsion system evaporates, leaving these components on the skin as the lipophilic components of the two-phase emulsion system are absorbed into the skin. The white residue on the skin contributes to the ashy appearance. The composition of the present disclosure is a one-phase lipophilic composition, lacking these compounds, provides a residue-free topical preparation.

In one example embodiment, the topical preparation for treating ashy skin comprises a prime base comprising of a butter base, aloe butter, avocado butter and caprylic acid. The topical preparation further comprises the prime base and cyclomethicone. In a further example embodiment, the topical preparation for treating ashy skin comprises a prime base comprising a butter base, aloe butter, avocado butter, caprylic acid and an essential oil, and cyclomethicone. Critical to the composition of the topical preparation is choosing the ingredients that melt close to skin temperature so that the preparation is liquid when applied and readily absorbable by the skin. The process of forming the mixture includes a tempering step described hereinbelow that creates a prime base close to skin temperature.

The topical preparation has a viscosity that ranges from a lotion to cream or ointment. The viscosity is selectively increased by adding petrolatum, up to four percent by weight to the preparation.

In one example embodiment, the butter base is preferably mango butter. In a further example embodiment, part or all the mango butter may be substituted with shea butter. The range of mango butter in the butter base is zero to one hundred percent, shea butter constituting the remainder of the butter base. In yet a further example embodiment, some or all of the shea butter may be substituted with cocoa butter.

The range of butter base in the topical preparation is 47 to 52 percent, preferably around 50 percent. Cyclomethicone is around 2 percent. The range of aloe butter is around 22 to 25, preferably around 23.5. The range of avocado butter is around 17 to 20, preferably about 18.6. The range of caprylic acid is around 2 to 3 percent preferably about 2.5. In this example embodiment, the essential oil has both therapeutic and fragrance properties. The range of essential oil is 1 to 4 percent preferably about 3.4 percent. Table 1 lists the ingredients of an example embodiment containing the preferred amounts.

TABLE 1

| Ingredient | Prime base | Lotion | Cream |
| --- | --- | --- | --- |
| Butter base | 51.0 | 50.0 | 48.0 |
| Aloe butter | 24.0 | 23.5 | 22.6 |
| Avocado butter | 19.0 | 18.6 | 17.9 |
| Caprylic acid | 2.5 | 2.5 | 2.4 |
| Essential oil | 3.5 | 3.4 | 3.3 |
| Cyclomethicone |  | 2.0 | 1.9 |
| Petrolatum |  |  | 4.0 |

Table 2 below shows another example embodiment that does not have an essential oil, the topical preparation for treatment of ashy skin of an individual that has sensitivity to perfumes and essential oils.

TABLE 2

| Ingredient | Prime base | Lotion | Cream |
| --- | --- | --- | --- |
| Butter base | 54.5 | 53.4 | 51.3 |
| Aloe butter | 24.0 | 23.5 | 22.6 |
| Avocado butter | 19.0 | 18.6 | 17.9 |
| Caprylic acid | 2.5 | 2.5 | 2.4 |
| Cyclomethicone |  | 2.0 | 1.9 |
| Petrolatum |  |  | 4.0 |

Table 3 below shows a further example embodiment with an essential oil providing a fragrance to the preparation.

TABLE 3

| Ingredient | Prime base | Lotion | Cream |
| --- | --- | --- | --- |
| Butter base | 53.5 | 52.4 | 50.3 |
| Aloe butter | 24.0 | 23.5 | 22.6 |
| Avocado butter | 19.0 | 18.6 | 17.9 |
| Caprylic acid | 2.5 | 2.5 | 2.4 |
| Essential oil | 1.0 | 1.0 | 1.0 |
| Cyclomethicone |  | 2.0 | 1.9 |
| Petrolatum |  |  | 4.0 |

A method of preparing an example embodiment of the topical preparation for treatment of ashy skin comprises selecting a plurality of lipophilic ingredients having the property of being in a liquid, molten state at around 37 degrees Centigrade.

A molten butter base is produced by melting with a heat source at least one plant-derived butter at around 58 degrees Centigrade until the butter base is in a molten state, at which point the heat source is removed. In one example embodiment, the plant-derived butter is mango butter, and in a further example embodiment, the plant-derived butter is shea butter. In yet another example embodiment, the butter base is a mixture of mango butter and shea butter. In yet a further example embodiment, the butter base comprises cocoa butter. In still a further example embodiment, cocoa butter is combined with mango butter and shea butter.

The step of heating the butter base to temperature above the melting point and removing heat is referred to as tempering. The heating step followed by a controlled cooling step has never been applied to the preparation of topical preparations, because topical preparations are generally two-phase emulsions and not single-phase mixtures. The unique selection of ingredients coupled with the tempering step produces the preparation that has the unique characteristics that are particularly effective in treating ashy skin, such as no residue from hydrophilic materials, liquid state at skin temperature and moisturizing ingredients that treat dry skin.

The butter base is heated to above the melting point to insure that all crystal forms of the fat are melted. Fats exist in nature in many polymorphic forms and the crystalline phase plays a large role in properties such as melting point, appearance and texture. Additional plant-derived butters, a liquid fatty acid and an essential oil are mixed into the molten butter base at low shear, forming an anhydrous slurry of a prime base. The addition of said additional butters and liquid fatty acid slowly cools the mixture in a controlled manner, controlling polymorphism in the slurry, the slurry cooling into a semi-solid state.

Heating the butter base above the melting point and gradually cooling the prime base by adding the ingredients that are at room temperature controls the crystallization process, minimizing polymorphism, to achieve a blend that has a melting point close to skin temperature. Polymorphic crystalline forms of fats have widely varying melting points. By reducing the formation of polymorphs that have an undesirable melting creates a product that consistently liquefies at body temperature.

In one example embodiment, the additional plant-derived butters further comprise aloe butter and avocado butter.

In another example embodiment, the fatty acid is caprylic acid.

In a further example embodiment, the essential oil is benzoin essential oil.

Before the prime base solidifies, a polysiloxane is added to the prime base mixture at low shear until completely blended, forming an essentially anhydrous, lipophilic topical preparation for treatment of ashy skin. In one example embodiment, the polysiloxane is cyclomethicone.

If a thicker preparation is desired, petrolatum is added to the mixture after the polysiloxane, mixing at low shear until a desired finished viscosity is achieved. The concentration of petrolatum does not exceed four percent.

Mango butter, also known by the INCI (International Nomenclature of Cosmetic Ingredients) name as *Mangifera Indica* Seed Butter, is classified as a skin conditioner. Mango butter is extracted from the kernels of the mango, which grows in the tropical climates of the world and rich in vitamins A, C and E. It is a natural sunscreen against ultraviolet rays. Mango butter melts close to skin temperature, but is a solid at room temperature. Mango butter is rich in oleic and stearic acids having a non-greasy feel and is easily absorbed into the skin.

Shea butter (INCI name *Butyrospermum Parkii* Butter), which can be substituted for some or all the mango butter, has similar properties. Shea butter is extracted from the kernels of the fruit of the shea nut tree. Shea butter melts close to skin temperature, but is a soft semi-solid at room temperature. Shea has only two polymorphic forms at skin temperature so that is more stable than many other fats and amenable to the tempering process. It is a natural sunscreen.

Cocoa butter (INCI name *Theobroma Cacao* (Cocoa) Seed Butter), which can be substituted for some of the shea butter, has similar properties to shea and mango butters. Cocoa butter has multiple polymorphic forms, the more stable β form having a melting point close to skin temperature. Cocoa butter is amenable to the tempering process to produce the more stable polymorphic forms.

Avocado butter (INCI name *Persea Gratissima* Butter) is produced by hydrogenating cold pressed avocado oil with other vegetable oils, creating a soft butter at room temperature. It is also a natural sunscreen.

Aloe butter (INCI name *Aloe Barbadensis* Leaf Butter) is an extract of aloe vera, aloe barbadensis, blended with other plant-based oils such as coconut oil. It is solid at room temperature, but melts on the skin.

Caprylic acid (octanoic acid, INCI name caprylic acid) is a hydrophobic, lipophilic organic acid that has antibacterial properties.

In one preferred example embodiment the essential oil is benzoin essential oil (benzoin oil, INCI name benzoin extract) is extracted from the resin of the *Styrax benzoin* tree. In addition to having a pleasant fragrance, it forms a protective film over skin. Typical components of benzoin essential oil are benzoic acid, cinnamic acids, benzyl benzoate, benzoic aldehyde, vanillin and coniferyl benzoate.

Cyclomethicone (INCI name cyclomethicone) is a polysiloxane. Although it is water dispersible, it is essentially water-free, containing less than 250 ppm of water. It promotes absorption of oils into top layers of epidermis and quickly evaporates, allowing the oils to remain in the skin.

Petrolatum (INCI name petrolatum) is a mixture of non-straight chain solid and high boiling liquid hydrocarbons, extremely nonpolar and hydrophobic, lipophilic semi-solid.

A method for treating skin having an ashy appearance comprises applying a topical preparation of lipophilic compounds in an amount sufficient to cover a surface of ashy skin requiring treatment. The topical preparation has a melting range around 37 degrees Centigrade and liquefies when it come in contact with the skin, the skin having a temperature at around 37 degrees Centigrade. The topical preparation is substantially absorbable by a plurality of top layers of skin and diminishes the ashy appearance of the skin when applied to said surface. The topical preparation leaves no visible solid residue when applied to the skin.

The topical preparation is occlusive, moisturizing the skin by retarding evaporation from the skin surface. The topical preparation has natural sunscreen properties. The preparation is applied at least daily.

The topical preparation has a viscosity greater than 5,000 cps at 25 degrees Centigrade and 5 rpm and it is a lotion at lower viscosity. Viscosity can be increased by the addition of petrolatum up to four percent so that the topical preparation has a viscosity of a cream or ointment when applied.

The topical preparation is applied to the surface of the skin on the limbs.

The topical preparation can be included in a kit that comprises the topical preparation, a brown sugar scrub for removing dead skin scales that add to the ashy appearance and a cyclomethicone spray mist for additional moisturization that forms a protective film after the cyclomethicone evaporates. Another example embodiment of the topical preparation further comprises a skin-lightening agent.

It is further understood that, although ordinal terms, such as, "first," "second," "third," are used herein to describe various components, and these components should not be limited by these terms. These terms are only used to distinguish one component from another component. Thus, "a first component," discussed above could be termed a second component without departing from the teachings herein.

In conclusion, herein is presented a topical preparation for treating ashy skin and a method of manufacture thereof. The disclosure is illustrated by example in the drawing figures, and throughout the written description. It should be understood that numerous variations are possible, while adhering to the inventive concept. Such variations are contemplated as being a part of the present disclosure.

What is claimed is:

1. A method of preparing a topical preparation for treating ashy skin, comprising:

selecting a plurality of plant-derived butters having a melting point around 37 degrees Centigrade, said plant-derived butters selected from the group consisting of mango butter, shea butter, cocoa butter, aloe butter and avocado butter;

melting at least one of said plant-derived butters with a heat source at around 58 degrees Centigrade to form a butter base in a molten state;

cooling the molten butter base by mixing at least one additional plant-derived butter and a liquid fatty acid into the molten butter base at low sheer to form an anhydrous slurry;

slowly cooling the anhydrous slurry in a controlled manner so as to control crystallization and polymorphism, resulting in polymorphs of said anhydrous slurry having a melting point around 37 degrees Centigrade;

cooling the anhydrous slurry into a semi-solid state; and mixing a polysiloxane into said cooled slurry at low shear until the mixture is completely blended to form said topical preparation.

2. The method of claim 1, further comprising mixing petrolatum into the cooled slurry at low shear until a desire finished viscosity is achieved, wherein the concentration of said petrolatum in the topical preparation does not to exceed 4%.

3. The method of claim 1, wherein the plurality of plant-derived butters is a mixture of mango butter and shea butter.

* * * * *